United States Patent
Lloyd

[11] Patent Number: 5,336,270
[45] Date of Patent: Aug. 9, 1994

[54] CONTINUOUS ONE-PIECE PROSTHESIS

[75] Inventor: Lawrence A. Lloyd, Lansing, Mich.

[73] Assignee: Wright & Filippis, Inc., Rochester, Mich.

[21] Appl. No.: 73,775

[22] Filed: Jun. 8, 1993

Related U.S. Application Data

[62] Division of Ser. No. 757,949, Sep. 12, 1991, Pat. No. 5,219,364.

[51] Int. Cl.$^5$ .............................. A61F 2/60; A61F 2/76
[52] U.S. Cl. ............................ 623/33; 623/55; 623/901; 264/222; 264/DIG. 30
[58] Field of Search ............... 623/27, 33, 35, 47–53, 623/55, 901; 264/222, 571, DIG. 30

[56] References Cited

U.S. PATENT DOCUMENTS

| | | | |
|---|---|---|---|
| 4,473,421 | 9/1984 | Gustafsson | 264/DIG. 30 X |
| 4,696,780 | 9/1987 | Hagglund | 264/222 |
| 4,941,212 | 7/1990 | Liff | 264/222 X |
| 5,004,477 | 4/1991 | Palfray | 623/53 |
| 5,108,454 | 4/1992 | Rothschild et al. | 623/33 |
| 5,116,381 | 5/1992 | Palfray | 623/33 |

FOREIGN PATENT DOCUMENTS

| | | | |
|---|---|---|---|
| 0806026 | 2/1981 | U.S.S.R. | 623/27 |
| 2067074 | 7/1981 | United Kingdom | 623/27 |

*Primary Examiner*—Randall L. Green
*Assistant Examiner*—D. Willse
*Attorney, Agent, or Firm*—Harness, Dickey & Pierce

[57] ABSTRACT

A one-piece continuous polymeric prosthesis is disclosed and taught. The prosthesis is intended for patients with a below-knee amputation. The one-piece socket-pylon-keel allows good energy storage and release for a superior feel during physical activities. The construction and the materials makes for a much lighter weight prosthesis than conventional types.

9 Claims, 3 Drawing Sheets

CONTINUOUS ONE-PIECE PROSTHESIS

This is a division of U.S. Pat. application Ser. No. 757,949, filed Sep. 12, 1991, now U.S. Pat. No. 5,219,364.

BACKGROUND OF THE INVENTION

A goal of prosthetists has been to reduce the weight of below-knee prostheses to reduce the energy and hence fatigue of the wearer. Reduction in weight, however, has to be balanced with the need to maintain sufficient weight-bearing strength to support the wearer during normal activity levels. The various materials used in the prior prostheses, such as wood and alloy metals (e.g. titanium), also tended to be rigid. This lack of material flexability did not allow significant energy storage and return during activities such as walking or running which, in turn, detracted from a natural feel to the wearer of the prosthesis.

The most common artificial leg for below-knee (b.k.) amputees are of a rigid nature. A solid shank will connect the socket, which mounts the artificial leg to the residual limb of the amputee, and the artificial foot. The shank is often made out of a rigid alloy such as one containing titanium or is made from shaped wood. The attachment of the shank to the artificial foot is also usually rigid. While advances have been made in the construction of artificial feet to provide energy-storing-/releasing systems, these advances primarily have the energy-storing system contained within the foot itself and not able to store energy through the shank due to the termination of the energy-storing system at the rigid foot-shank union. The energy-storing system can take the shape of a C-shaped plastic spring running from the ankle through the arch and terminating toward the ball of the foot. In the case of the metal shanked artificial leg, the system can weigh in the range of 3½–4 pounds. In the case of the wood shank, the artificial leg can weigh on the order of 3 pounds.

The Flex-Foot® artificial leg produced by Flex-Foot, Inc., Irvine, Ca., is an example of the currently available artificial leg which exhibits a more natural dynamic action by using a flexible energy storing pylon and keel, the flexible pylon and keel is formed from a strip of laminated reinforced composite which is mechanically attached to the socket descending down to form the pylon and continuing on to form the keel of the artificial leg. Applying pressure to the Flex-Foot® artificial leg (e.g. walking on it) causes flexation of the pylon and foot which acts as a spring to store energy and release it during walking or running movements. While the Flex-Foot® artificial leg allows for more natural-feeling movement due to its energy storing and returning action than prior art rigid artificial legs and while lighter than other prior art legs made of titanium and/or wood, its weight (on the order of approximately 2½ pounds) can be of concern to geriatric patients, as well as more active patients.

For geriatric patients, artificial legs of these weight ranges can cause discomfort and reduced activity. Oftentimes small savings in weight can produce great results due to the nature of walking with its repeated activities of lifting the leg. Likewise, for younger amputees, the increased weight can cause increased fatigue during exercise and slower times when competing e.g. in races. The prior art also suffers from a lack of flexibility which would allow sufficient energy storage and return to approximate the dynamics involved in athletic activities such as running.

The invention provides a prosthesis with improved energy storage and return action. The invention also provides a prosthesis that is substantially lighter than known prostheses while still offering sufficient weight-bearing strength. The invention further provides a prosthesis that is readily capable of having its energy storage and flexation action modified. The invention provides a durable prosthesis which provides an energy storage and return action for the wearer. The invention provides a prosthesis which can be easily fabricated by trained personnel using readily available orthopaedic materials and commonly available equipment.

From the subsequent detailed description taken in conjunction with the accompanying drawings and subjoined claims, other objects and advantages of the present invention will become apparent to those skilled in the art.

SUMMARY OF THE INVENTION

This invention is directed primarily to an artificial leg or prosthesis for a below-knee amputee and is fabricated out of a continuous sheet of plastic such as a polypropylene-polyethylene blend.

A test or trial prosthesis is fitted to the amputee to determine the proper sizing and fit of a socket as well as the relative orientation of points such as the ball of the foot and heel of the foot to the terminus of the residual limb. A sole and heel cushion is selected to approximate the outline of the natural foot. A keel mold is placed on the surface of the heel and sole cushion and is attached to a male model for the socket sized from the test or trial prosthesis to allow proper fit. The keel mold has an outline similar to that of the sole and heel cushion. Raised ribs extend from the ankle area of the keel mold. The keel mold is attached to the socket model by a steel mandrel. The model of the socket is aligned relative to the heel and sole cushion to replicate the alignment arrived at previously through use of a test prosthesis. A sheet of softened thermoplastic is molded over the entire assembly forming a socket where molded over the model of the socket, a pylon were molded over the steel mandrel, and a keel were molded over the keel mold. The raised ribs of the keel mold will form corresponding ridges of plastic which are designed to stiffen the keel and/or the keel-pylon transition. Vacuum is applied to the inside of the wrapped sheet to vacuum form the plastic sheet to the mold surfaces.

After cooling, the keel mold, mandrel and model of the socket are removed, the plastic edges of the prosthesis are then trimmed, and the sole and heel cushion attached to the underside of the keel. The prosthesis may be further finished in the manner normally used for an endo-prosthesis, e.g., a cosmetic covering put on the outside. The prosthesis is attached to the patient in the conventional manner by the insertion of the residual limb into the socket and the placement of a rubber cuff around both the socket and limb.

The resultant product is a one-piece continuous prosthesis, much lighter in weight than other known prostheses, weighing on the order of 20 ounces or less. Even lighter artificial limbs can be constructed for geriatric patients where the load-bearing requirements are not as critical. Resulting prostheses also allow for an energy storage and return function during walking by controlled flexing of the keel in combination with the pylon. The pylon also allows limited flexure from side to side or laterally, more closely mimicking the action of a natural limb below the knee. The pylon can be adjusted for foot position, eversion, inversion and rotation along with plantar or dorsi-flexation and pylon flexibility. The keel has an interchangeable heel wedge. The stiffness of the keel and/or pylon can also be adjusted by removal of material to reduce rigidity. Keel stiffness can be increased by the addition of material such as a stiffening beam to the keel. Keel and pylon stiffness can be increased by insertion of an additional keel-pylon assembly. Reheating the plastic allows changes to be made in the alignment of the prosthesis.

DETAILED DESCRIPTION INCLUDING PREFERRED EMBODIMENT

The preferred embodiment of the invention is a below-knee prosthesis. A test or trial prosthesis is first fitted to the patient. The trial prosthesis may be of any conventional known design and is used primarily to establish certain reference points for the definitive, i.e., final, prosthesis. Included in the reference points to be determined by the trial prosthesis are the fit of the socket to the residual limb and the location and form of the distal foot. These fitting techniques are conventional techniques and commonly known to prosthetists for fitting of prostheses.

Figure 1:
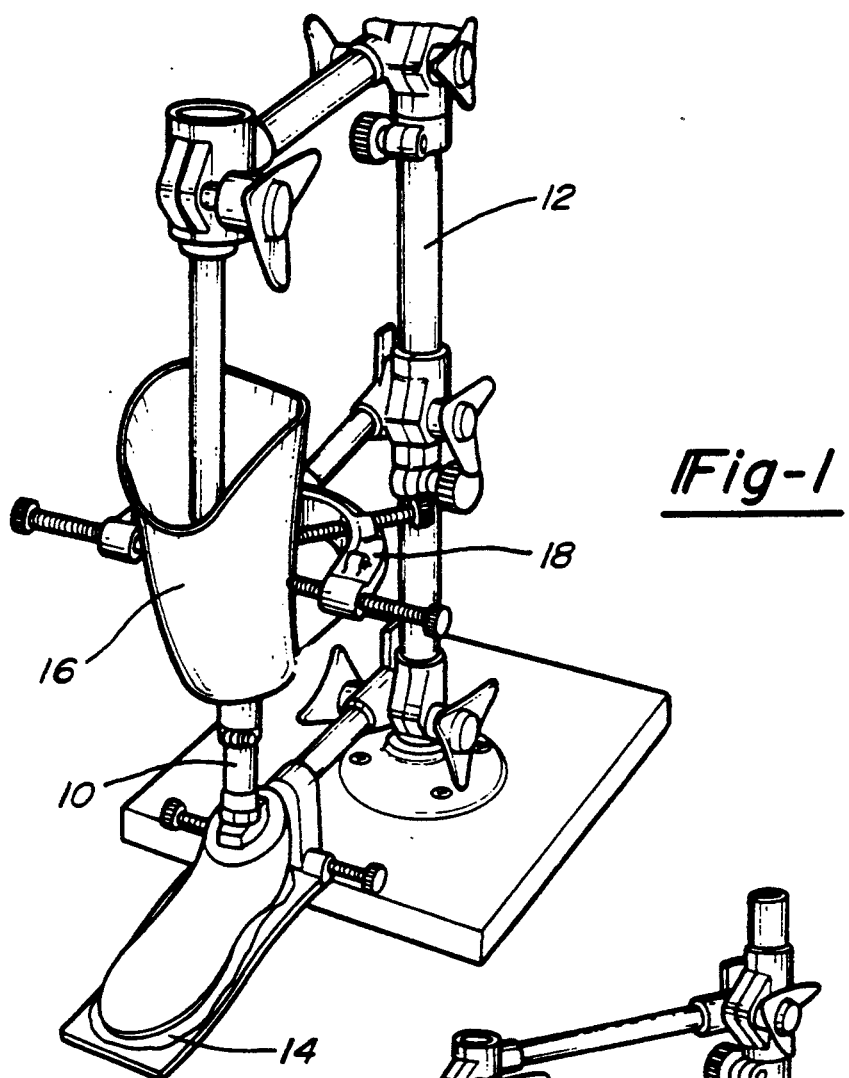
FIG. 1 is a perspective view of a test prosthesis mounted in a vertical alignment jig.

Referring to FIG. 1, once the fit and alignment of the trial prosthesis (10) has been finalized, it is placed in a vertical alignment jig (12) and a plaster impression is formed of the distal foot (14). The socket (16) is secured to the vertical alignment Jig (12) by collar (18). The inside of the socket (16) of the trial prosthesis (10) is alginated to form a male mold by casting alginate (a casting product from COE Laboratories, Inc., Chicago, Ilinois 60621) into the interior of the socket (16) to form the alginate impression (20).

Figure 2:
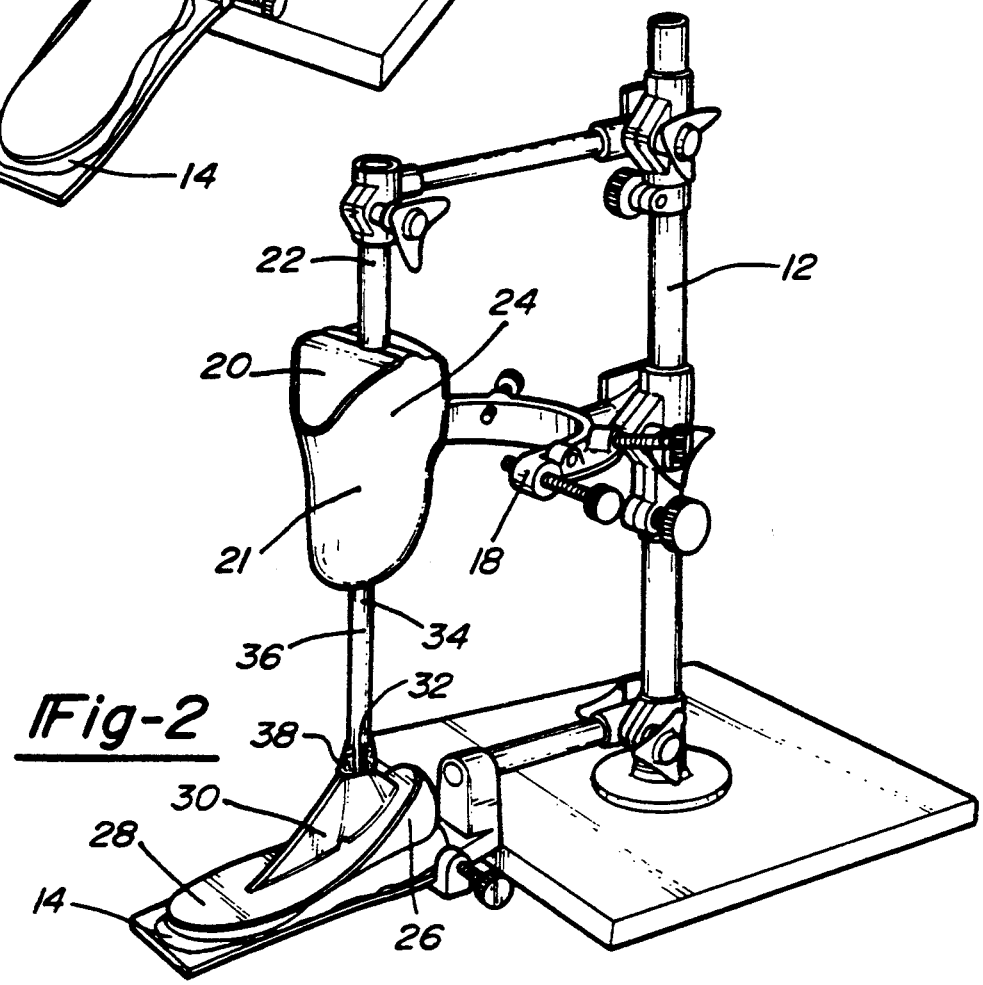
FIG. 2 is a perspective view of a mold of the invention mounted in a vertical alignment jig.

As shown in FIG. 2, the alginate impression (20) is locked into alignment on the vertical alignment jig (12) using the pipe (22) of the jig to maintain alignment of the alginate impression (20) relative to the plaster impression of the distal foot (14). The alginate impression (20) is then removed from the socket being careful to maintain the reference points which determine alignment. The alginate impression (20) is then splinted with plaster of paris bandages to form female socket mold (21) over the alginate impression (20). A buildup area (24) is created using the plaster bandages to allow the collar (18) on the vertical alignment jig (12) to secure and reference the plaster female mold socket (21) on the jig (12). These referencing points in the buildup area are preferably established at the patellar tendon level.

The collar (18) is then repositioned in the vertical alignment jig (10) and the plaster covered alginate impression (20) is locked into and referenced to the vertical alignment jig (12) by the reference points in the buildup area (24) of the female socket mold (21). The alginate impression (20) and pipe (22) are now removed and the alignment of the remaining plaster female socket mold (21) is maintained solely by the reference points established by the interface of the collar (18) with the buildup area (24).

A prosthetic sole and heel combination (26) is matched with and placed on the plaster impression of the distal foot (14). The preferred sole and heel combination prosthesis is manufactured by Otto Bock Orthopaedic Industries, Inc., 3000 Xenuim Lane North, Minneapolis, Minnesota 55441. Depending on the manufacturer and size of the sole and heel combination, some modification may be needed when transferring from one sole and heel combination prosthesis to another. It is important that the heel and ball orientation of the sole and heel combination (26) should not be altered from that established through fitting of the trial prosthesis to the wearer and recorded in the plaster impression of the distal foot (14). Finishing technique of the resulting prosthesis can also vary the size of the sole and heel combination (26) selected. As an example, cosmetic covers may add a full-size over the internal sole and heel combination prosthesis.

A keel form (28) is then positioned onto the sole and heel combination prosthesis (26). The keel form (28) will serve as a mold over which the keel portion of the prosthesis will be formed. Therefore, the keel form (28) should be sized to match the outline of the sole and heel combination (26) which is substantially the outline of a natural foot. The keel form (28) can also be selected to have a rib mold (30) so that the resultant prosthesis will have stiffening ribs cast into it. The resultant ribs may be sized to strengthen the area where the keel transitions into the pylon to resist fractures or failure at that juncture. The stiffening ribs will affect the stiffness of the resultant keel and hence its energy storage and return properties. The weight and activity level of the patient should be assessed in determining the proper stiffness of the resultant keel. While stiffness of the final keel and prosthesis as a whole can be modified as explained below, proper selection of a keel form with a sufficiently large rib mold (30) allows sufficient stiffness to be cast into the keel. The exact stiffness characteristic can be later modified as explained below by removing material or, if necessary, adding material to the prosthesis. The rib mold should be sized so that the resultant rib would end at the approximate location of the metatarsal heads in a natural foot. By terminating the rib at the approximate location of the metatarsal heads, the keel is more likely to flex at that location, thus approximating the flexing characteristics of a natural foot.

The desired socket-pylon relationship is then established in both the sagittal plane and the coronal plane.

The socket-pylon intersection point (34) is translated to a spot on the distal end of the plaster female socket mold (21) which will establish the socket-pylon intersection point (34) marking the upper end of the pylon where it is integrated into the socket. A ¾ inch vertical hole is then cut in the distal end of the plaster female socket mold (21) at the socketpylon intersection point (34). A length of ¾ inch metal pipe constituting a mandrel (36) is secured to the keel form (28) at the point established for the lower end of the pylon at the keelpylon intersection point (32) and is inserted through the ¾ inch hole in the distal end of the plaster female socket mold extending approximately 2–3 inches into the interior of the socket. The top end of the mandrel should be flared or textured to provide adequate bonding strength of the mandrel to the material which will be cast inside of the plaster female socket mold.

The thermoplastic material used to form the final prosthesis shrinks as it cools and allowance must be made for the dimensional change of the thermoplastic from its heated size to its cooled size. In addition, the keel form (28) will be removed from the final prosthesis and allowance must be made for the absence of its thickness when adhering the sole and heel combination (26) to the underside of the resultant keel. Therefore, the plaster socket should be raised relative to the mandrel by an amount sufficient to compensate for both the shrinkage of the thermoplastic material and the absence of the keel form (28) in the final product. These two factors result in a 3/16-¼ inch length discrepency along the vertical axis and the socket should be raised by this amount during this stage of alignment transfer. The inside of the plaster female socket mold (21) is then coated with a mold release agent such as soap or silicone oil. The plaster female socket mold is then filled with plaster to create the definitive socket male mold.

The junction of the mandrel (36) and keel form (28) should be secured and reinforced to eliminate eversion-/inversion, dorsi-plantar flexion or rotational alignment deviation. In an effort to secure the pylon keel junction, the mandrel-keel form junction is reinforced by a reinforcing band (38) formed by example from a composite of epoxy or polyester resin and fiberglass particles. Other methods of achieving the necessary reinforcement can include mechanical or adhesive means to build up the area of the mandrel-keel form junction (32). The result should provide a mold surface for the resultant prosthesis which gives a generous transition surface from the mandrel (36) to the proximal portion of the keel form (28).

The resultant assembled model is removed from the vertical alignment jig. The plaster female socket mold is removed, leaving the cast in place plaster socket form attached to the mandrel. Care should be taken to avoid impact or stress on the keel form which might deform or misalign the keel form. The article is then smoothed to remove any surface irregularities and/or sharp edges which may be replicated in the final article.

Figure 3:
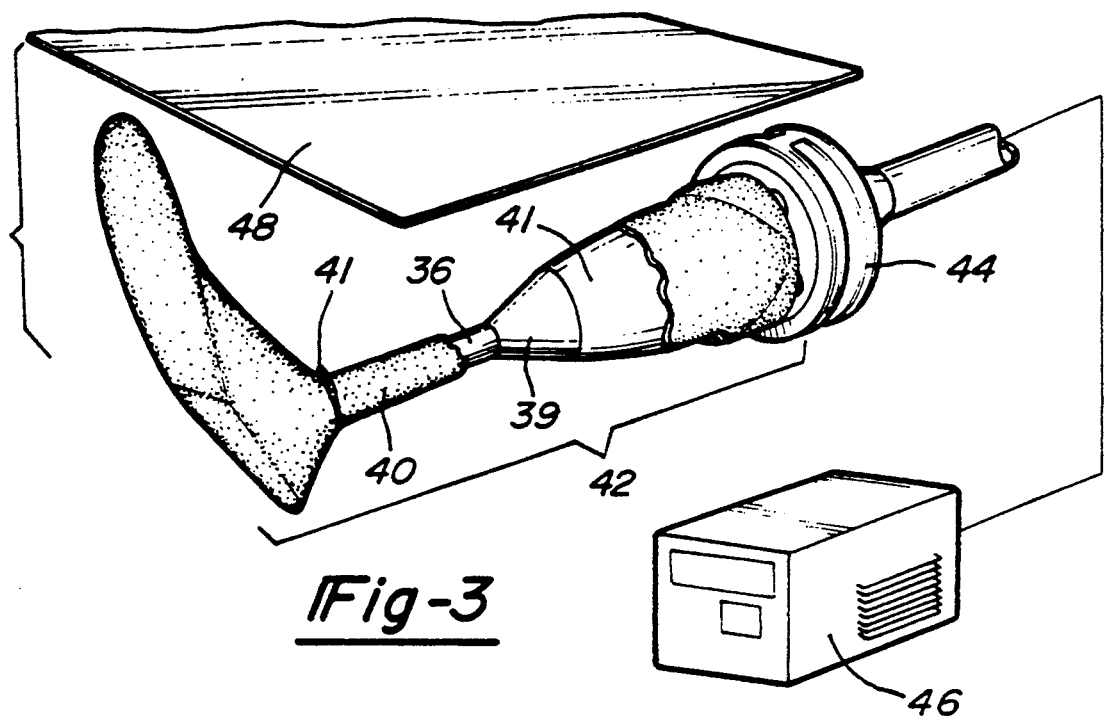
FIG. 3 is a perspective view of a mold of the invention ready to have plastic vacuum-thermoformed over it.

Referring to FIG. 3, a truncated cone (39) is fashioned around the mandrel (36) and male socket mold (41) intersection to provide a smoothly transitioned mold surface. The truncated cone is preferably fabricated from Pelite ®. Pelite ® is a registered trademark of Durr-Fillauer Medical, Inc., P.O. Box 1678, Chattanooga, Tennessee 37401. Similar material can be substituted.

A mold release agent should then be applied to the assembled model to facilitate removal of the model from the fabricated final prosthesis. In the preferred embodiment, a nylon stocking or stockinette (40) is pulled over the entire assembled mold (42) and knotted off at the top as seen in FIG. 3. The nylon stocking reduces sticking of the material to the model as well as maintaining air passageway between the prosthesis forming plastic and the model during vacuum forming as discussed below. Where the nylon stocking (40) does not conform to the assembled model surface, such as transition points from the keel form to the mandrel and/or the mandrel to the socket, the nylon can be tied down with fine thread (41). The assembled model (42), encased in the nylon stocking (40), is then horizontally mounted to a jig (44) operably connected to a vacuum source (46).

A sheet of the plastic material (48) for the final prosthesis is then cut to proper size to allow fitting over and encasing the entire assembled model (42). The preferred material for fabricating the prosthesis is a thermoplastic copolymer consisting of polypropylene and polyethylene. The most preferred material is a copolymer sheet consisting of 95 percent polypropylene and 5 percent polyethylene such as sold by Maramed Precision Corp., 2480 West 82nd Street, Hialeah, Florida 33016. The thickness of the polymer sheet is to be determined by the strength desired in the ultimate article. This, in turn, depends upon the weight and activity level of the patient. It has been found that ¼ inch thick sheet material has been suitable for moderately to highly active patients. Less active patients and/or patents of reduced weight can have successful results with a prosthesis formed from thinner materials. Such patients can also benefit from the further reduction of weight obtained from using thinner materials.

The copolymer sheet (48) is then heated in an oven to 330°-355° F. Care should be taken so that the sheet (48) is not overheated and loses the integrity of the copolymer mix. The assembled model is horizontally secured in the jig (44) with the toe portion of the keel form pointing up. The sheet of heated copolymer is draped over the top of the horizontal assembled model and then pressed to conform to the assembled model. Care should be taken to have thickness of the sheet remain uniform, i.e., not thinned due to stretching. This is especially important in the segment formed over the mandrel (36) which becomes the pylon. The edges of the copolymer sheet are brought together along the back of the assembled model and pressed together to form a flanged seam along the posterior portion of the assembled model. A vacuum is then applied by the vacuum source (46) between the copolymer sheet (48) and the assembled model (42) to more closely conform the copolymer sheet to the assembled model in a vacuum-forming procedure. It has been found that the nylon stocking (40) functions to maintain air passages along the surface of the assembled model. These air passages reduce the chance of bubbles forming in the final prosthesis by pockets of air trapped between the copolymer sheet (48) and the assembled model.

Additional reinforcement means such as a stiffening beam (51) (shown in FIG. 4) can be added to the keel form to stiffen the front portion of the resultant keel and create a stiffer toe lever. One method of increasing the stiffnesses is to mount additional polymeric material onto the keel form so that it is fused to the polymer sheet when it is wrapped around the assembled model. It has been found that a horseshoe-shaped piece of copolymer made from the same material as that of the final prosthesis can be placed on the keel form with the open ends of the horseshoe placed approximately one inch anterior to the metatarsal heads. This additional material will considerably increase the stiffness of the toe lever when it is encased in the final prosthesis. Additional reinforcing means can include spring steel or carbon graphite composites encased in the polymer addition to form springs or stiffeners in the keel.

Once the copolymer has cooled, the assembled model encased in plastic is removed from the fixture. The plaster male model around which the socket has been formed is broken out and removed. The mandrel and keel form are also removed, as is the nylon stocking.

Figure 4:
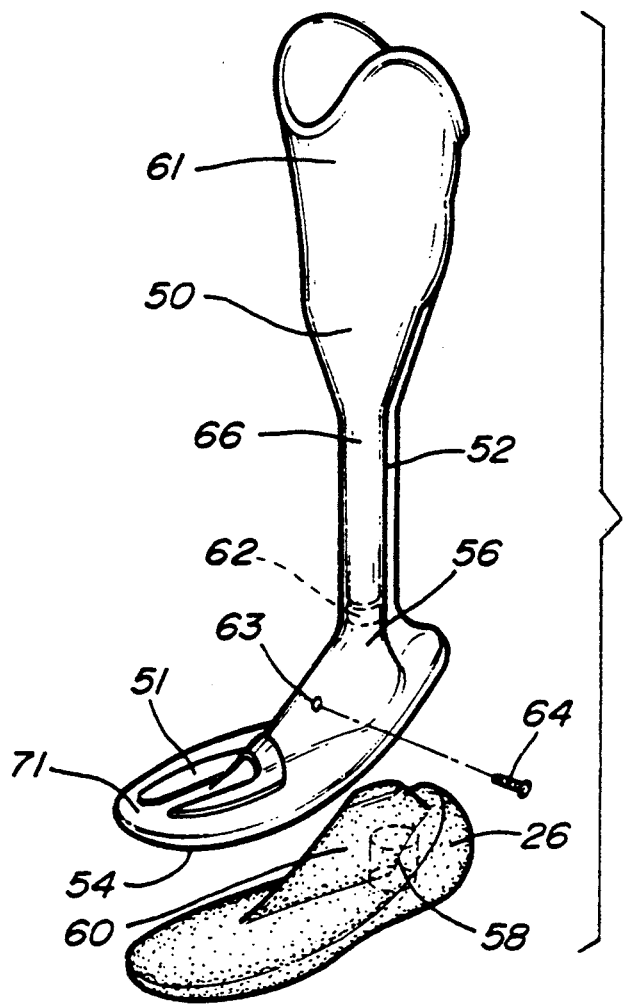
FIG. 4 is an exploded perspective view partially in section of a prosthesis in accordance with the present invention.

Referring to FIG. 4, the resultant prosthesis (50) is a one-piece polymeric prosthesis with the additional stiffening beam (51) being secured thereto. The edge of the socket is then trimmed to remove excess material and burrs or sharp edges. The posterior flange seam (52) is also trimmed. Care should be used so as not to remove the entire posterior flange seam as the flange portion performs a stiffening function and reduces flexibility of the pylon in the anterior or posterior direction. Additional material from the flange can be removed to increase flexibility. The keel rim (54), the material depending downward from the border of the keel, i.e., the material that is formed over the sides of the keel form, should be trimmed, but some material depending downward should be left intact. The keel rim increases the rigidity of the keel and serves to position and secure the sole and heel combination prosthesis (26).

A plug (62) is inserted into the pylon in the ankle area. The plug may be made of clay and should be positioned above the area corresponding to the natural ankle as at (56). Approximately 30 grams of material that forms a rigid foam such as IPOS R-120 rigid foam from IPOS North America, Inc., P.O. Box 320, Niagra Falls, NY 14304, is prepared and poured into the inverted ankle cavity. The heel and sole combination prosthesis (26) is placed over the reacting foam. The bolt hole (58) of the heel and sole combination prosthesis is used to vent excess foam as the mixture reacts. A funnel may be placed through the bolt hole (58) to vent excess foam during reaction. The resultant foam bonds itself to the combination sole and heel prosthesis (26) while remaining relatively unbonded to the copolymer sheet. The combination sole and heel prosthesis with the attached rigid foam can now be removed. The now rigid foam has formed a mast (60) which aids in securing the combination sole and heel prosthesis to the heel and pylon. The plug (62) is removed. The mast may be coated with nylon stockinette to help eliminate rubbing noise. The mast as attached to the combination sole and heel prosthesis is inserted into the bottom of the keel. A ⅛ inch hole (63) is drilled through prosthesis (50) and the mast (60) through the anterior portion of the ankle. A mechanical fastener (64) such as a pin or screw is secured through the hole (63) holding the mast and hence the sole in place. The ¾ inch circular hole in the distal end of the socket left by the removal of the mandrel is also plugged such as by Pelite ®.

The prosthesis may be further finished in a manner normally used for endoskeletal prostheses. The cosmetic cover as sold by the Flex-Foot ® Company has been found to work successfully. Care should be taken so that the combination sole and heel prosthesis has been properly sized to allow the cover to be fitted.

The resultant prosthesis (50) is much lighter than conventional below-knee prostheses and is particularly useful for geriatric wearers, especially those with reduced strength. The prosthesis is free from structural material other than the copolymer material itself. A typical prosthesis of the present invention sized for an adult male of vigorous activity is on the order of less than 20 ounces. The reduced weight gives less resistance to movement, allowing the wearer to maintain activity for longer periods of time.

The resultant prosthesis is also useful for vigorous amputees who find that the energy-storing and releasing action of the keel (71) integrated with the pylon (60) which itself is integrated with the socket (61) has a more natural feel during running and walking. The keel can flex, especially in the region of the metatarsal heads, giving a more natural flexion akin to a natural foot. The ability of the keel to flex along various lines combined with its footprint approximating the natural foot adds to its stabilizing characteristics. The keel is also able to store energy while flexing. The flexing of the pylon also serves an energy storage and return function during walking or running. The pylon can store energy along its inter length in part due to its integration with the socket as one piece. The keel and pylon can cooperatively flex due to their continuous nature. The pylon and keel can also flex laterally during activity more closely approximating the flexing of the natural ankle. The vigorous amputee also benefits from the lighter weight, especially in competitive events.

Should alignment correction or realignment be necessary, the pylon section (66) of the prosthesis may be aligned by reheating. If rotational corrections are necessary, the ¾ inch mandrel is reinserted. A ¾ inch solid rubber mandrel may be inserted to make positional alignment changes. The rubber mandrel will prevent collapse or deforming of the pylon cylindrical cross-section as changes are made to the heated prosthesis pylon. Care should be exercised to maintain the cylindrical cross-sectional shape of the pylon during alignment changes.

Figure 5:
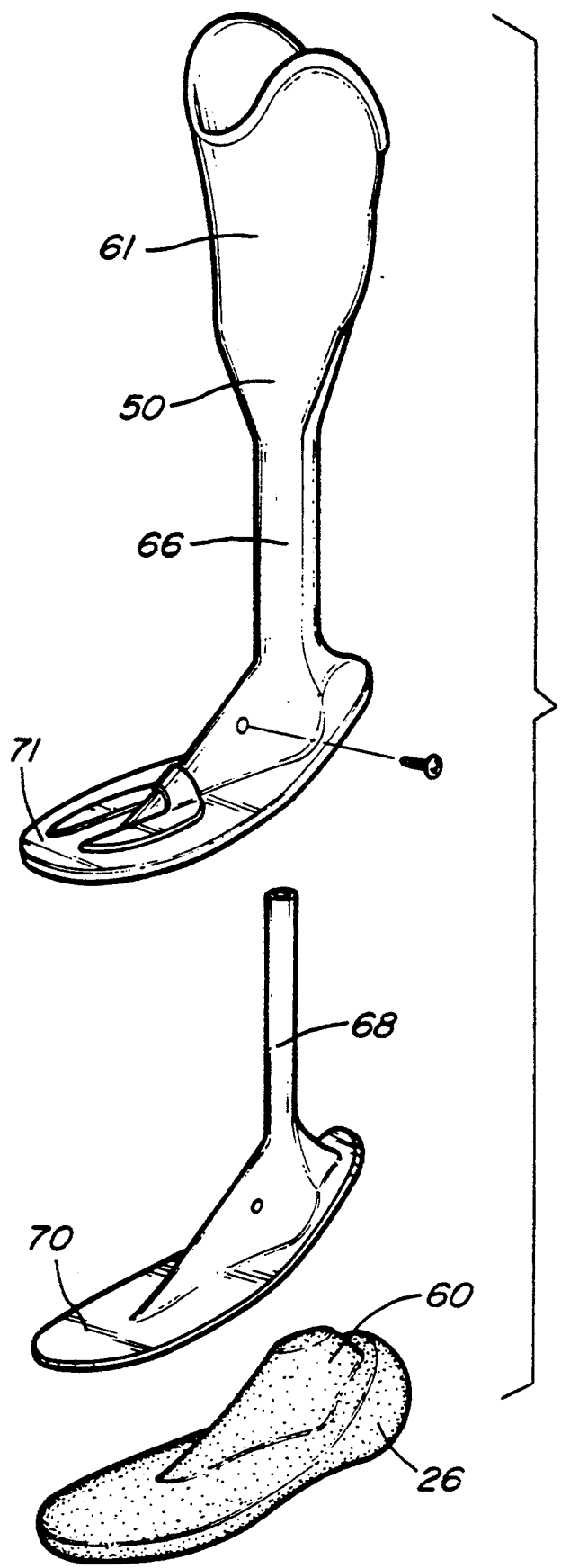
FIG. 5 is an exploded perspective view of an alternate embodiment of the invention.

Referring to FIG. 5, a further feature of the present invention is the use of a sport pylon (68) providing for modification of the dynamics of the prosthesis. The sport pylon is a secondary pylon and keel assembly particularly useful for vigorous amputees. The sport pylon is sized to fit within the interior of the pylon (66) of the prosthesis (50) with the keel portion (70) of the sport pylon fitting within the keel (71) of the prosthesis. After removing the combination sole and heel prosthesis (26) and mast (60), insertion of the sport pylon alters the dynamics of the prosthesis by providing a second spring layer in the keel section. This may be useful for providing more energy storage in, for example, the toe section. The sport pylon also stiffens the pylon (66) of the prosthesis (50) to reduce flexing. The sport pylon can also be formed so that the portion of the keel corresponding to the natural toe is plantar flexed. The sport pylon should have its own combination sole and heel prosthesis (26) dedicated to its use to insure proper height of the total prosthesis. The hardness of the heel dedicated to the sport pylon can differ from the heel normally used with the prosthesis depending on the activity the sport pylon is intended for. As an example, the hardness of the heel can be changed usually by increasing its hardness. The position and outline of the sole and heel combination of the sport pylon can also be altered from the sole and heel combination used with the prosthesis. The activities that the sport pylon is intended for may also call for no heel wedge of the sole and heel prosthesis (26) to be used. Amputees participating in sprinting events may prefer this, as there is very little heel strike in such activity. The sport pylon allows the amputee to wear his prosthesis throughout the day at a comfortable walking alignment with a soft heel and flexible keel-pylon combination. Upon arriving at the court, track, or ballfield, the sport pylon may be inserted to alter the dynamics of the prosthesis for a more realistic energy-returning sensation from the ball of the foot and toes when running or jumping.

EXAMPLE

A 28-year-old male patient weighing approximately 175 pounds and with a vigorous activity level had been fitted with a laminate/endo/Seattle foot prosthesis for his medium length below-knee amputation. The subject was very active, participating in running, sprinting, and playing volleyball, among other sports. The subject was fitted with a prosthesis of the present invention. The complete prosthesis weighed approximately 1¼ pounds (20 ounces). Over the first three to four days, the prosthesis was broken in for a slight reduction in the toe lever or stiffness of the toe portion of the keel. The prosthesis is reinforced over the forefoot with a second layer of ¼ inch copolymer sheet in the form of a horseshoe. As a result of the initial break-in, the toe has exhibited an upward migration of a minimal amount and the prosthesis as a whole shows no adverse reaction to the weight and activity level of the subject. The subject has previously worn "energy-storing" feet and more conventional types of foot such as the SAFE (Stationary Attachment Flexible Endoskeletal), SACH (Solid Ankle Cushioned Heel), and Greissenger feet. The subject describes action of the keel and pylon dynamics as a mid-point between a Seattle® foot and a Flex-Foot®.

While the above detailed description describes preferred embodiments of the present invention, it will be understood that the present invention is susceptible to modification, variation and alteration without deviating from the scope and fair meaning of the subjoined claims.

What is claimed is:

1. A method of forming a prosthesis for a below-knee amputee comprising:
   providing a model of the residual limb providing a keel mold to form a keel;
   connecting said residual limb model with said keel mold with a pylon mandrel in an aligned relation to form an assembled prosthetic model;
   forming a single polymeric sheet over said assembled prosthetic model; removing said assembled prosthetic model; and
   forming a continuous prosthesis having a hollow pylon portion, a keel portion having a substantially planar platform with a top and bottom surface which are substantially parallel to one another and a heel and toe, and a limb receiving portion.

2. The method of claim 1 further comprising securing resilient sole means to the portion formed over said keel mold.

3. The method of claim 1 further comprising removing polymeric material after forming to modify the stiffness of the resultant prosthesis.

4. The method of claim 1 wherein said forming step further comprises thermo-vacuum forming said polymeric sheet to said assembled prosthetic model.

5. The method of claim 3 further comprising attaching keel stiffening means to increase the resistance to flexing of the area formed by the keel mold.

6. The method of claim 1 further comprising attaching a stiffening beam to the surface formed by said keel mold to provide selectively removable material for adjusting the flexation of said surface formed by said keel mold.

7. The article formed by the method of claim 1 wherein the alignment of said keel to said socket is capable of modification after initial formation.

8. The method of forming a prosthesis comprising,
   proving a model of a trial prosthesis fitted to a wearer;
   thermo-vacuum forming a single sheet of substantially homogeneous copolymer material over said model to produce a continuous one-piece prosthesis;
   removing said model from the formed prosthesis;
   forming a continuous prosthesis having a hollow pylon portion, a keel portion having a substantially planar platform with a top and bottom surface which are substantially parallel to one another and a heel and toe, and a limb receiving portion; and
   selectively removing copolymer material to adjust the stiffness of the prosthesis.

9. The prosthesis formed by the method of claim 8 wherein said prosthesis is substantially free of structural material non-homogeneous to the copolymer.

* * * * *